(12) United States Patent
Beller

(10) Patent No.: US 7,758,575 B2
(45) Date of Patent: Jul. 20, 2010

(54) APC DEVICE

(75) Inventor: Jurgen Beller, Gomaringen (DE)

(73) Assignee: ERBE Elektromedizin GmbH, Tübingen (DE)

( * ) Notice: Subject to any disclaimer, the term of this patent is extended or adjusted under 35 U.S.C. 154(b) by 749 days.

(21) Appl. No.: 11/571,850

(22) PCT Filed: Jul. 8, 2005

(86) PCT No.: PCT/EP2005/007404

§ 371 (c)(1),
(2), (4) Date: Jan. 9, 2007

(87) PCT Pub. No.: WO2006/005534

PCT Pub. Date: Jan. 19, 2006

(65) Prior Publication Data

US 2007/0233058 A1    Oct. 4, 2007

(30) Foreign Application Priority Data

Jul. 12, 2004  (DE) ........................ 10 2004 033 616
Jul. 30, 2004  (DE) ........................ 10 2004 037 084

(51) Int. Cl.
*A61B 18/12* (2006.01)
(52) U.S. Cl. .......................... 606/40; 606/49
(58) Field of Classification Search ............. 606/34–40, 606/49
See application file for complete search history.

(56) References Cited

U.S. PATENT DOCUMENTS

| 6,113,596 A  * | 9/2000 | Hooven et al. ................. 606/42 |
| 6,565,558 B1 * | 5/2003 | Lindenmeier et al. ......... 606/34 |
| 2003/0069576 A1 | 4/2003 | Tanrisever |
| 2004/0044339 A1 * | 3/2004 | Beller et al. ................... 606/34 |

FOREIGN PATENT DOCUMENTS

| DE | 19706269 | | 9/1997 |
| EP | 0353178 | A2 | 1/1990 |
| WO | 9301758 | A1 | 2/1993 |
| WO | 0012019 | | 3/2000 |

\* cited by examiner

*Primary Examiner*—Linda C Dvorak
*Assistant Examiner*—Benjamin Lee
(74) *Attorney, Agent, or Firm*—Dickstein Shapiro LLP

(57) ABSTRACT

An APC device to simultaneously operate a plurality of instruments for argon plasma coagulation. In order to enable simultaneous connection and operation of several instruments, the APC device provides several instrument hubs to connect the plurality of instruments and to connect a control device to all instrument hubs. The control device controls the amplitude of a high-frequency voltage and operates the APC device such that, on actuation of at least one actuation means and generation of at least one actuation signal, the high-frequency voltage is interrupted for a defined duration and then the high-frequency voltage is set to the ignition voltage level and, after ignition of the plasma on all of the APC instruments for which the actuation means is actuated, the high-frequency voltage is set to the operational voltage level.

6 Claims, 3 Drawing Sheets

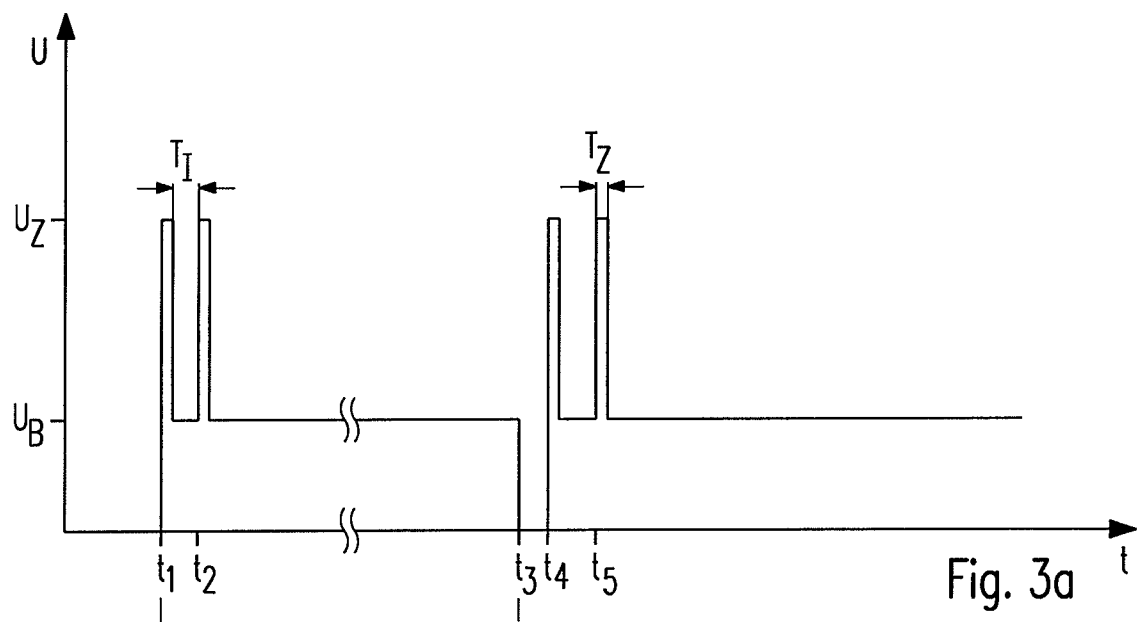
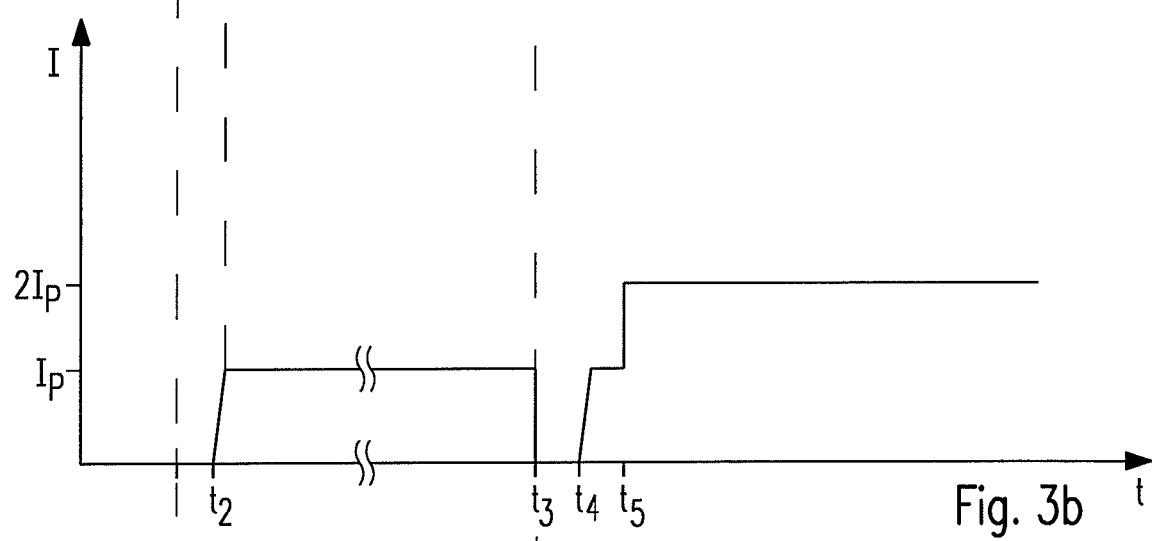
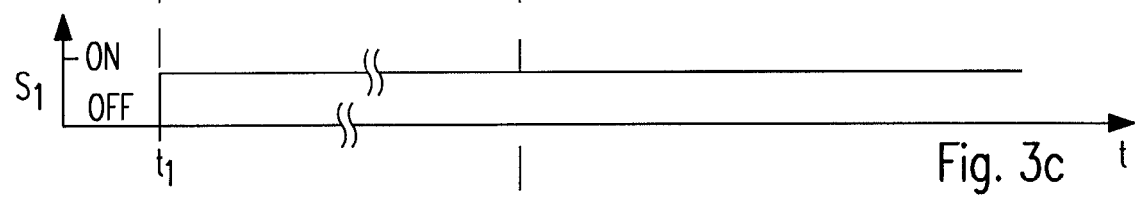
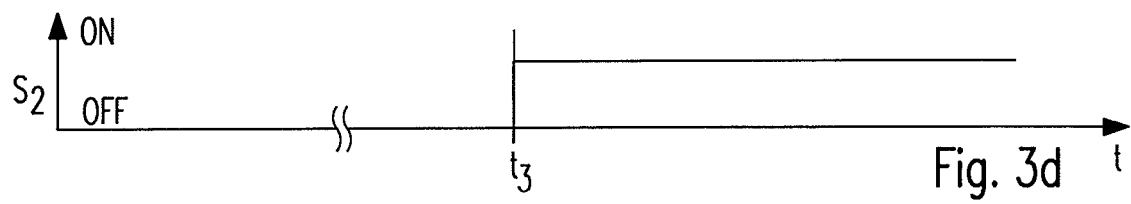

APC DEVICE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The disclosed embodiments relate to an argon plasma coagulation (APC) device for operating instruments for argon plasma coagulation.

BACKGROUND OF THE INVENTION

APC devices for the operation of instruments for argon plasma coagulation are known, wherein other inert gases besides argon can be used. Reference is made herein only by way of example to WO 93/01758.

In large-scale operations, namely when several surgeons are working on one patient, a separate APC device must be available to each of the surgeons to enable him to connect the instrument he is currently using. This is often not possible, not only for cost reasons, but also because it leads to highly constricted space conditions.

BRIEF SUMMARY OF THE INVENTION

The object of the disclosed embodiments is to provide an APC device that can operate several instruments simultaneously.

In accordance with the disclosed embodiments an APC device for the operation of a plurality of instruments for argon plasma coagulation (each instrument including an actuation means for production of an actuation signal upon actuation), comprises a high-frequency generator to produce a coagulation current, a control device to control an amplitude of a high-frequency voltage output by the high-frequency generator by setting the high-frequency voltage at an ignition voltage level in response to an actuation signal and by automatically setting the high-frequency voltage at an operational voltage level once a plasma has been ignited, wherein the ignition voltage level is higher than the operational voltage level; a first instrument hub connecting a first instrument of the plurality of instruments to the control device; and a second instrument hub respectively connecting a second instrument of the plurality of instruments to the control device.

The control device allows simultaneous connection and the simultaneous operation of the plurality of instruments such that, when the actuation means of one of the plurality of instruments is actuated to generate the respective actuation signal, the high-frequency voltage is interrupted for a predetermined interruption period $(t_4-t_3)$ and is then set to the ignition voltage level $(U_L)$ and, after ignition of the plasma on all of the instruments for which the actuation means is actuated, the high-frequency voltage is then set to the operational voltage level $(U_B)$.

Therefore, the aim of the disclosed embodiments is that, during operation of an instrument, when a further instrument is activated operation of the first (already operating) instrument is briefly interrupted and then a plasma is ignited or re-ignited simultaneously on both instruments. This interruption only negligibly disrupts the currently working surgeon because the plasma may occasionally be extinguished anyway if the correct minimum distance required for working is exceeded.

The interruption duration is preferably set to a very short time, namely less than 100 ms and preferably less than 20 ms. This duration is then so short that it is not even visually perceived by the surgeon.

In conventional devices, the amplitude of the coagulation current, for example, is measured to ascertain whether a plasma has been ignited. The high-frequency voltage is then switched back from the ignition voltage to the operational voltage when the real current component exceeds a specific, preset value or another identifying feature of the arc (e.g. the complex resistance of the plasma or a resulting specific signal form) is present.

In one embodiment, the high-frequency voltage is switched back from the ignition voltage to the operational voltage when the current amplitude corresponds to the sum of all coagulation currents that flow to the instruments with the actuation elements actuated after ignition of each plasma. Therefore, an "attempt" is made to ignite until all (actuated) instruments produce a plasma.

To this end, an instrument counter can be provided and configured so that the number of existing actuation signals is recorded, the sum of the coagulation currents before or on arrival of a further actuation signal is detected and the high-frequency voltage is then switched back to the operational voltage when the coagulation current from the high-frequency generator corresponds to the number after arrival of the further actuation signal compared with the number before arrival of the further actuation signal. Therefore, which coagulation current has to flow in total when a plasma is present at all actuated instruments is "estimated". It goes without saying that it is also possible to realize this "estimation" via the aforementioned further measures.

The ignition voltage is preferably maintained in the form of an ignition pulse for a predetermined duration and is then reduced to the operational voltage. After it has dropped to the operational voltage, a further ignition pulse is then produced if the plasma has not been ignited on all instruments with actuated actuation elements. This measure serves the purpose of safety, to avoid excessive introduction of energy during the presence of the ignition voltage.

In a further embodiment, the further instrument hubs are not arranged in the APC device itself, but in an additional housing for connection to the APC device. As a result, (if required) existing APC devices can be converted to devices configured according to the disclosed embodiments and accordingly may be used by several users.

Various embodiments are described below by way of example and with reference to the accompanying drawings.

BRIEF DESCRIPTION OF THE DRAWINGS

FIGS. 3a-3d are graphs which schematically show voltage and current profiles.

DETAILED DESCRIPTION OF THE INVENTION

In the following description, the same reference numbers are used to denote identical parts and those that have an identical effect.

Figure 1:
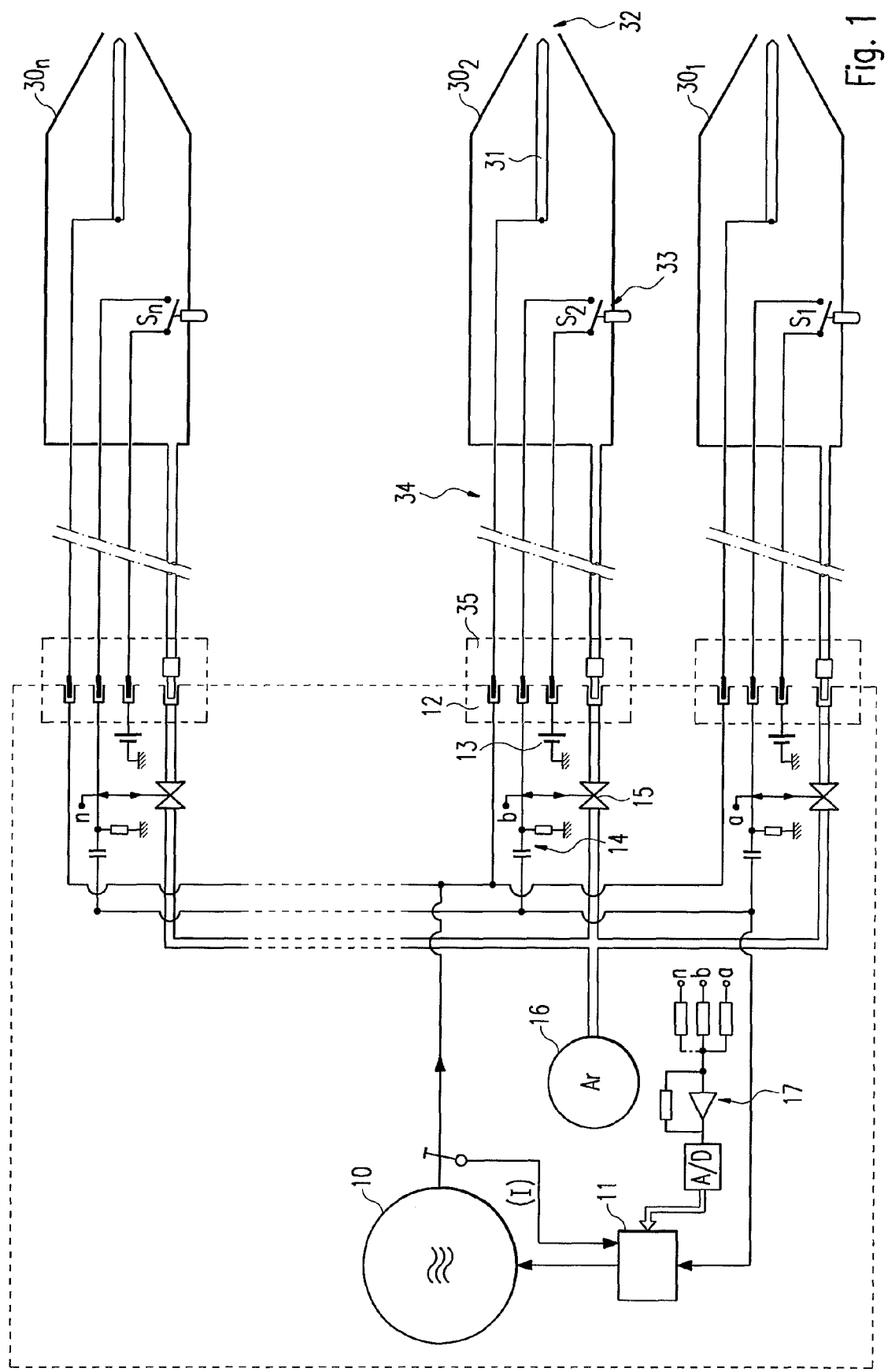
FIG. 1 a schematic diagram of a first embodiment.

As shown in FIG. 1, the instruments $30_1$ to $30_n$ comprise hollow bodies with a distally arranged nozzle 32, in whose proximity an electrode 31 is arranged in the hollow body. An actuation switch 33 for actuation of the switches $S_1$ to $S_n$ is provided as the actuation element. The electrode 31, the switches $S_1$ to $S_n$ and the interiors of the instruments $30_1$ to $30_n$ are connected to an instrument hub 12 on the APC device via a connecting lead 34 and an instrument connector 35. From there, the leads are routed on to a high-frequency generator 10, through a valve 15 to an argon source 16 and a control device 11, which controls (open or closed loop) the generator 10 and possibly also the argon source (in particular its pressure).

The above depiction is merely an equivalent depiction and does not show the exact structure of the known APC devices. In particular the devices $30_1$ to $30_n$ can be structured differently, e.g. as probes, wherein the actuation switches 33 are usually configured as foot switches. This outline depiction will, however, suffice for an understanding of the disclosed embodiments.

Each of the instruments $30_1$ to $30_n$ is connected via one instrument connector 35 respectively to one of several instrument hubs 12. In order to generate an actuation signal (this also is only a very schematic depiction), a voltage source 13 is provided and, closing the circuit between the voltage source 13 and the switch $S_1$ to $S_n$, is a resistor of a high-pass filter 14 with a capacitor connected at the output end to the capacitors of the further instrument hub 12. Together, these output hubs of the capacitors or of the high-pass filters 14 are connected to an input of the control device 11.

The input ends of the high-pass filters 14 are also connected to a counter device 17 that comprises an adder(-subtracter) and an A/D converter.

This arrangement makes it possible on the one hand for the control device 11 to obtain information about the time when one of the actuation switches 33 is closed (this information is present at the output of the high-pass filter 14) and, on the other hand, how many actuation switches are currently actuated. Moreover, when the appropriate actuation switch 33 is actuated, the valve 15 for each instrument $30_1$ to $30_n$ is opened so that argon gas can only flow to the applicable instrument $30_1$ to $30_n$, or can only flow out of its nozzle 32, when the associated actuation switch 33 is actuated.

The (basic) operating principle of this arrangement is described below with reference to FIGS. 3a-3d, wherein 3a shows the course of the output amplitude U of the high-frequency generator 10 and thus the course of the voltage between the electrode 31 and the patient as a function of time. FIG. 3b shows, over the same time, the current amplitude I of the output current of the high-frequency generator 10 and FIGS. 3c and 3d show switched states of two switches $S_1$ and $S_2$ on two instruments $30_1$ and $30_2$.

According to FIG. 3c, the switch $S_1$ is closed via the associated actuation switch 33 at the time $t_1$. The actuation signal is passed on to the control device 11, which raises the output voltage of the high-frequency generator 10 to the ignition voltage $U_Z$ (see FIG. 3a). After a predetermined interval $T_Z$, the output voltage of the high-frequency generator 10 is returned to the operational voltage $U_B$ (e.g. from 4 kV to 2 kV). It is assumed here that still no plasma has been ignited on the instrument $30_1$ at this time. Accordingly, the output current of the high-frequency generator 10 at this time is still at zero (see FIG. 3b). After a waiting interval $T_1$, a further ignition pulse is issued, which ends again after the interval $T_Z$, i.e. the output voltage of the high-frequency generator 10 is returned again to the operational voltage $U_B$. At this time, according to the example shown here, a plasma (or arc) is ignited so that the output current from the high-frequency generator 10 rises to a level $I_P$ (see FIG. 3b).

If the actuation switch 33 of a further instrument $30_2$ is now actuated at a later time $t_3$ and the associated switch $S_2$ is closed (see FIG. 3d), the high-frequency generator 10 is deactivated, and so its output current and output voltage drop to zero. After a predetermined interval, an ignition operation as described above is again initiated at a time $t_4$. In this case, the chosen interval $t_3$-$t_4$ is very short, thus avoiding (substantially disrupting work with the instrument $30_1$.

Now, in the situation shown in FIG. 3, it is assumed that, at the time $t_4$, a plasma has been ignited only on one of the instruments $30_1$ or $30_2$. Therefore, the current flowing out of the high-frequency generator 10 still corresponds to the current $I_P$ that is present at only one instrument (as in the period $t_2$ to $t_3$) when a plasma is present. Accordingly, the control device 11 generates a further ignition pulse at the time $t_5$. Here, it is now assumed that a plasma has been ignited on both instruments $30_1$ and $30_2$ so that the current rises to the value $2I_P$ at the time $t_5$. By the value of this current amplitude, the control circuit, to which is fed the amplitude of the output current of the high-frequency generator 10, can ascertain whether a current is being obtained that corresponds to the number of instruments $30_1$ to $30_n$ with actuation switches 33 actuated.

Also in relation to this description, it must be mentioned that it is merely very schematic. In particular, the current amplitudes are reproduced only very schematically because differing currents (depending on the distance from the tissue) are needed for the various connected instruments. It is also possible to determine the number of ignited plasmas in another way. What is important, however, is that ignition pulses are generated for the length of time that is needed for a plasma to be present at all instruments whose actuation elements have been actuated.

Figure 2:
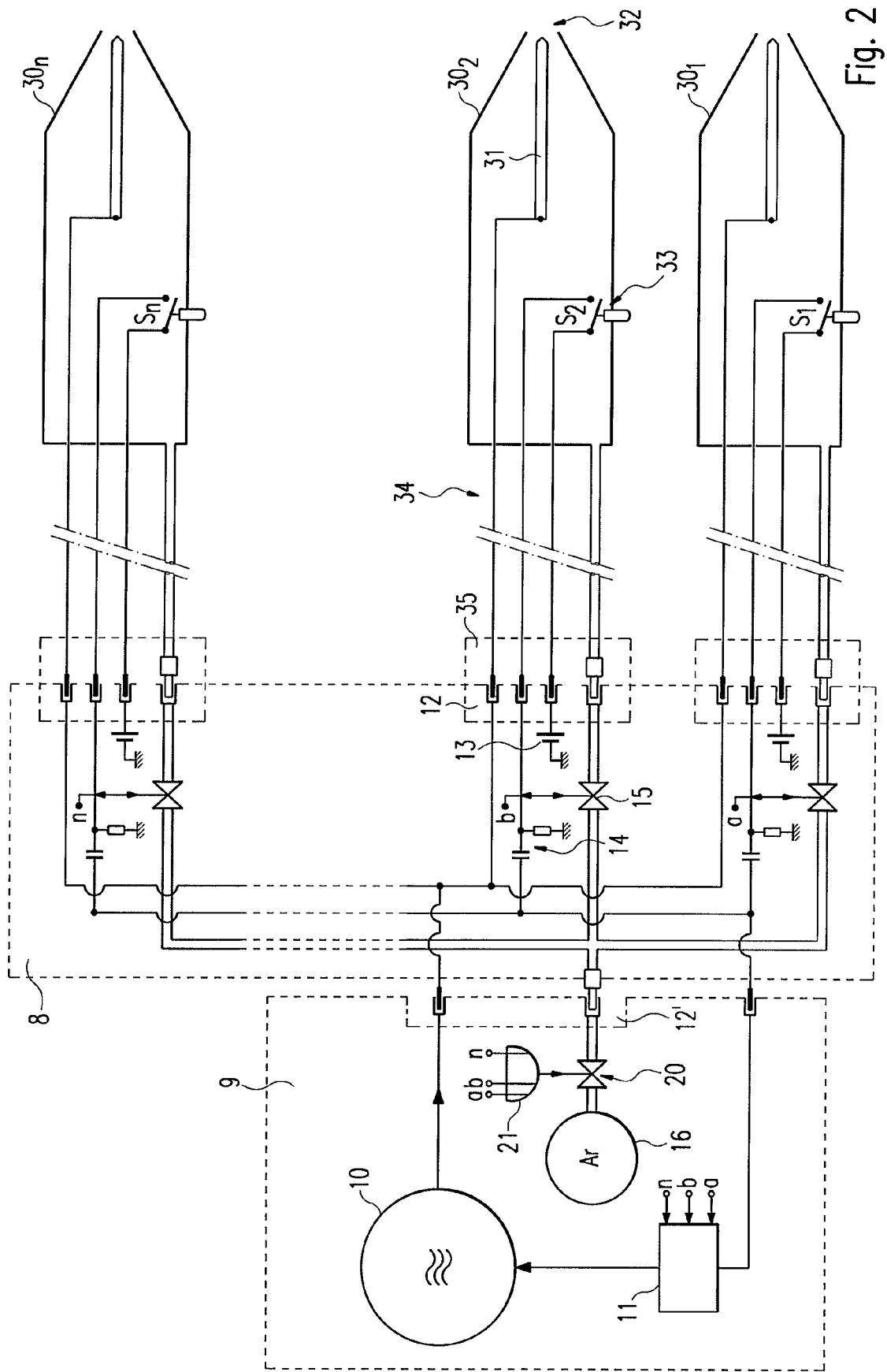
FIG. 2 a schematic diagram of a second embodiment which includes an additional housing.

The embodiment shown in FIG. 2 initially differs from the one shown in FIG. 1 in that the large number of instrument hubs 12 is housed in an additional housing 8, which is then connected to a generator housing 9 via appropriate connectors.

Furthermore, in the case of the embodiment shown in FIG. 2, a central valve 20 is provided in the generator housing that is connected to the inputs of the high-pass filters via an OR gate and opens only if at least one of the actuation elements 33 has been actuated. This arrangement (with one central valve) can naturally also be provided in the embodiment shown in FIG. 1. Equally, the counter device 17 can also be provided in the embodiment shown in FIG. 2.

The invention claimed is:

1. An APC device to operate a plurality of instruments for argon plasma coagulation, each instrument comprising an actuation means for production of an actuation signal upon actuation, the APC device comprising:

a high-frequency generator that produces a coagulation current;

a control device that controls an amplitude of a high-frequency voltage output by the high-frequency generator by setting the high-frequency voltage at an ignition voltage level in response to an actuation signal and by automatically setting the high-frequency voltage at an operational voltage level once a plasma has been ignited, wherein said ignition voltage level is higher than said operational voltage level;

a first instrument hub connecting a first said instrument of the plurality of instruments to said control device; and a second instrument hub respectively connecting a second instrument of the plurality of instruments to said control device, and wherein said control device allows simultaneous connection and simultaneous operation of said plurality of said instruments such that, when said actuation means of one of said plurality of instruments is actuated to generate the respective actuation signal, the high-frequency voltage is interrupted for a predetermined interruption period and is then set to said ignition voltage level and, after ignition of the plasma on all of said instruments for which the actuation means is actuated, is then set to said operational voltage level.

2. The APC device according to claim 1, wherein said predetermined interruption period is less than 100 ms.

3. The APC device according to claim 1, wherein a current amplitude of said coagulation current produced by the high-frequency generator is measured and the high-frequency voltage is switched from said ignition voltage level to said operational voltage level when the current amplitude corresponds to a number of individual coagulation currents respectively flowing to each of said instruments for which the actuation means is actuated after the ignition of the plasma of each of said instruments for which the actuation means is actuated.

4. The APC device according to claim 3, further comprising:

an instrument counter device connected to said control device and that detects the number of actuation signals present and that ascertains the number of individual coagulation currents before and on arrival of a further actuation signal, in order that said high-frequency voltage is switched back to said operational voltage level when the number of individual coagulation currents from the high-frequency generator corresponds to the number of actuation signals after the arrival of said further actuation signal compared with the number of actuation signals before the arrival of said further actuation signal.

5. The APC device according to claim 3, wherein the ignition voltage level is maintained as an ignition pulse for a predetermined duration and, after dropping to said operational voltage level, a further ignition voltage level pulse is generated if the plasma has not been ignited on all instruments for which the actuation means is actuated.

6. The APC device according to claim 1, wherein said first and second instrument hubs are arranged in a housing separate from and connectable to a housing for other elements of the APC device.

\* \* \* \* \*